United States Patent [19]

Audibert et al.

[11] 4,413,063

[45] Nov. 1, 1983

[54] PROCESS FOR OPERATING HIGHLY EXOTHERMIC REACTIONS

[75] Inventors: Francois Audibert, Ecully; Andre Sugier, Rueil Malmaison; Hugo Van Landeghem, Oytier Saint Oblas, all of France

[73] Assignee: Institut Francais du Petrole, Rueil-Malmaison, France

[21] Appl. No.: 324,758

[22] Filed: Nov. 25, 1981

[30] Foreign Application Priority Data

Nov. 25, 1980 [FR] France .............................. 80 25031

[51] Int. Cl.$^3$ .......................... C07C 1/04; C07C 27/06
[52] U.S. Cl. .................................... 518/700; 518/713; 518/714; 518/715; 518/701
[58] Field of Search ............... 518/700, 713, 714, 715, 518/701

[56] References Cited

U.S. PATENT DOCUMENTS

| | | | |
|---|---|---|---|
| 2,167,004 | 7/1939 | Pier et al. ............................ | 518/700 |
| 2,318,602 | 5/1943 | Duftschmid et al. ............... | 518/700 |
| 2,535,060 | 12/1950 | Gresham ............................ | 518/700 |
| 2,692,274 | 10/1954 | Kolbel et al. ..................... | 518/700 X |
| 4,031,123 | 6/1977 | Espino et al. ....................... | 518/700 |

FOREIGN PATENT DOCUMENTS 283499 7/1928 United Kingdom ................ 518/700

*Primary Examiner*—Howard T. Mars
*Attorney, Agent, or Firm*—Millen & White

[57] ABSTRACT

Improved process for reacting carbon monoxide with hydrogen. The reactant gases circulate downwardly in admixture with a liquid phase of inert diluent through a fixed bed catalyst. The superficial velocity of each of the gas phase and the liquid phase is at least 1.5 cm per second, preferably 3 to 20 cm per second. The products are hydrocarbons, for example methane, or alcohols, for example methanol, depending on the catalyst.

11 Claims, 1 Drawing Figure

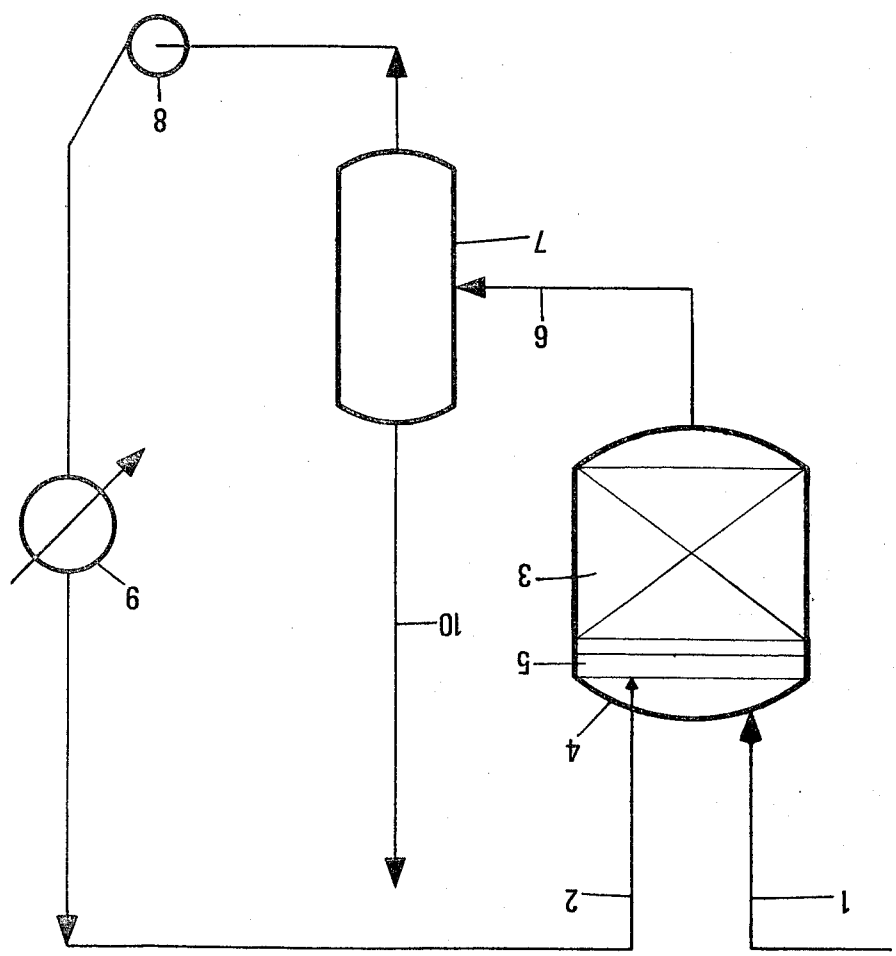

PROCESS FOR OPERATING HIGHLY EXOTHERMIC REACTIONS

BACKGROUND OF THE INVENTION

The present invention relates to the carrying out of a fast and strongly exothermic catalytic reaction between two or more gaseous compounds. A typical example thereof is the manufacturing of methane from a mixture of CO and $H_2$ according to the overall stoichiometry:

$$CO + 3H_2 \rightleftharpoons CH_4 + H_2O$$

or the manufacturing of alcohols, particularly methanol, according to the overall stoichiometry:

$$CO + 2H_2 \rightleftharpoons CH_3OH$$

or otherwise the manufacturing of hydrocarbons heavier than methane or alcohols heavier than methanol.

These reactions are so strongly exothermic (the adiabatic temperature rise, when synthesizing methane, is about 17° C. per each 1% of conversion) that in most cases they require the use of a diluent, associated or not with a thermal exchange through the wall of the reactor. Several processes have been designed which make use, as diluent, either of the output gaseous mixture which is then partially recycled, with or without steam injection, or of a liquid, for example a hydrocarbon, which, under the operating conditions, can remove the heat by sensible heat and evaporation.

A high recycle rate of the liquid and the condensed vapor ensures the thermal stability of the reactor.

In the processes operated with a liquid, the catalyst is normally used either as a suspension of fine particles or as unmoved particles of a fixed or ebullated bed.

It is important that the catalyst be immersed in the liquid to ensure a good liquid-solid contact everywhere, thereby avoiding the formation of a dry zone in the reactor, which zone could be responsible for an insufficient thermal stability; very high temperatures can be attained in that dry zone, since the reaction can take place entirely in the gas phase therein. A number of techniques have been proposed, wherein a continuous liquid phase is circulated upwardly, the catalyst being used as a suspension, as an ebullated bed or as a fixed or moving bed. These techniques have however serious disadvantages: substantial attrition of the catalyst takes place, due to the displacement of the catalyst particles, even with a so-called fixed bed; fine catalyst particles can be carried away from the reaction zone, resulting in racing of the reaction in the separators, the exchangers or at any other part of the plant; finally the productivity of the catalyst bed is relatively low.

A technique using a downflow stream (trickle flow) of gas and liquid has been proposed (U.S. Pat. No. 2,167,004). This technique has not been used on an industrial scale, since, in that case, the reactants flow through the reactor in such a way that the gas phase is the continuous phase and the liquid flows as thin streams or drops. This type of flowing leads easily to the formation of dry zones, resulting in thermal instability.

Thermal instability can be sometimes tolerated by the catalyst for a certain time, when it is weak. However it unavoidably results in a shortening of the catalyst life.

OBJECTS OF THE INVENTION

One object of the present invention is to provide a process which obviates the disadvantages of both processes with a liquid upflow stream and a liquid downflow stream. For example, the following results are obtained:

heat stability of the reactor, resulting in an extended life of the catalyst, absence of catalyst displacement, resulting in negligible attrition and formation of fines, and no carrying away of fine particles of catalyst from the reaction zone.

An increase of the catalyst bed productivity is observed, thus allowing a reduction in the reactor size for the same capacity of production.

SUMMARY OF THE INVENTION

The present process consists of downwardly circulating the gaseous reactants and a liquid phase of diluent through a fixed bed catalyst, the superficial velocities of the gas phase and of the liquid phase each being at least 1.5 centimeters per second, preferably at least 3 centimeters per second. A preferred velocity range is from 3 to 20 cm/s.

BRIEF DESCRIPTION OF THE DRAWING

The FIGURE illustrates an embodiment of the present process.

DETAILED DISCUSSION OF THE INVENTION

Superficial velocity is intended to mean the ratio of the volumic flow rate of the liquid or gas phase, under the temperature and pressure conditions selected for the reaction, to the reactor cross-section, the latter being considered free of catalyst.

Although the mechanism of the invention is not fully understood, it seems that the flow of gas and liquid is of a different type than observed for lower circulation velocities, for example those conventionally used in the hydrotreatment of hydrocarbons.

The optimum superficial velocity depends in part on the size of the catalyst particles and the physico-chemical properties of the liquid. It seems however practically independent of the superficial velocity of the gas.

The catalyst particles have usefully an average diameter of 0.5 to 10 mm, particularly 1 to 6 mm and preferably 1.5 to 3 mm.

The catalyst is any catalyst known to be effective for the contemplated reaction. For example, when manufacturing methane, a nickel catalyst (the preferred catalyst) can be used, or otherwise a ruthenium, iron, cobalt, molybdenum, rhenium or noble metal catalyst.

The catalyst can be supported or not. Examples of carriers are silica, alumina, silica-alumina, aluminates, thoria, zirconia, magnesia, silicon carbide, rutile, carbon or metallic carriers, for example as plates or filaments.

When manufacturing alcohols, for example methanol, anyone of the catalysts known for this reaction can be used, for example a catalyst comprising copper, chromium, iron, cobalt or other transition metals, or oxides of these metals.

The diluent is a liquid which, under the reaction conditions, does not substantially take part in the reaction and has no detrimental effect on the latter. It is preferably a hydrocarbon or a hydrocarbon fraction (an oil cut), for example a gas oil fraction, a fuel oil fraction, a molten paraffin wax, an aromatic oil, a silicone oil, a liquid tetrafluoroethylene polymer or a heavy alcohol or a mixture of heavy alcohols having, for example, from 10 to 20 carbon atoms.

If the catalyst is affected by sulfur, a previously desulfurized hydrocarbon fraction is preferably used.

The so-obtained liquids have usually a density of 0.4 to 2 g/cm$^3$ and a viscosity of 0.05 to 10 centipoises (0.05 to 10 mpa.s) under the conditions of the reaction, these values being illustrative and not mandatory.

Although the stoichiometrical proportions for the reaction are 3 moles of $H_2$ per mole of CO (synthesis of methane) or 2 moles of $H_2$ per mole of CO (synthesis of methanol), other ratios can be used. For example, when working with a hydrogen deficit, the water formed can react with excess carbon monoxide generate hydrogen, according to the well-known reaction $$CO + H_2O \rightleftarrows CO_2 + H_2$$

From 1.5 to 4 moles of hydrogen per mole of carbon monoxide can thus be used.

The best results of the process are obtained with a good liquid distribution at the top of the reactor obtained by means of devices well known in the art and whose choice is not part of the invention. By way of example, a spraying device can be used, or a distribution plate in strictly horizontal position with a relatively high number of perforations.

The temperature and pressure are selected within conventional ranges, depending on the selected catalyst and reaction. The temperatures are usually between 200° and 400° C. and the pressures between 1 and 20 MPa.

EXAMPLES 1 TO 4

The catalyst used in the following examples 1 to 4 was prepared from alumina balls having a 2 mm average diameter, a pore volume of 80 ml per 100 g including 10 ml/100 g of pores of diameter larger than 0.8 μm, a specific surface of 60 m$^2$/g and a bulk density of 0.6.

These alumina balls are impregnated with an aqueous solution of nickel nitrate and then dried at 120° C. for 12 h and calcined in air at 380° C. for 4 h.

The concentration of the nickel nitrate solution is such that the nickel oxide content (as NiO) of the catalyst is 15% b.w. after the above calcination.

The catalyst is activated in the reactor by treatment with a mixture of 5% $H_2$ and 95% $N_2$ by volume, circulating at a space velocity (VVH) of 500 volumes per volume of catalyst per hour for 20 h at a temperature increasing progressively from 330° to 430° C.

In the following examples 1 to 4, illustrated by the drawing a synthesis gas (duct 1) and a liquid phase (duct 2) are circulated downwardly through 1.25 dm$^3$ of the above catalyst (3) arranged as a fixed bed in a reactor (4). The liquid is uniformly distributed through a perforated plate (5). The effluent is discharged through duct (6). The liquid phase is separated from the gas phase, at the outlet of the reactor, in the separator (7) and continuously re-circulated by pump (8), through the cooling exchanger (9) and line 2. Conversely the gas is not re-circulated; it is discharged through line 10 and analyzed. It can be subjected to condensation to collect the formed products.

In the following, the results are given as conversion rate of the reactants (CO+$H_2$) when the latter are used in stoichiometrical proportions, or as conversion of CO in the other cases. The selectivity is defined as the ratio of the resultant methane to the methane which should theoretically have formed (converted reactants).

EXAMPLE 1

The reactor has a diameter of 4 cm and a height of 1 meter. The synthesis gas consists of a mixture of 25% carbon monoxide with 75% hydrogen.

The gas injection rate is 6 m$^3$/h in the standard conditions of temperature and pressure, corresponding to a superficial gas velocity of 4.2 cm/s at 330° C., temperature of the experiment, and at 7 MPa.

The liquid phase is a $C_{10}$-$C_{16}$ desulfurized paraffinic hydrocarbon cut having a specific gravity at 20° C. of 0.85 (about 0.6 at 330° C.) and a viscosity at 330° C. of about 0.12 centipoise (0.12 mPa.s). Its feed rate at 20° C. is about 140 l/h, thus about 200 l/h at 330° C., corresponding to a superficial velocity of 4.5 cm/s and a VVH of 156.

The discharged liquid is re-circulated. The formed light products, particularly methane, are periodically or continuously separated, as are other light hydrocarbons and water.

Under these conditions, the carbon monoxide conversion is 97% and the selectivity to methane 95% in the initial state. After 2000 h of run, the conversion is 88% and the selectivity 96%.

EXAMPLE 2

(Comparison)

The feed rate of the synthesis gas as well as the catalyst volume, are the same as in example 1 but the reactor has an internal diameter of 7.3 cm; the height of the catalyst bed under these conditions is 37.6 cm.

The superficial gas velocity is 1.3 cm/s and the superficial liquid velocity 1.35 cm/s at 330° C. and 7 MPa.

Under these conditions of an average temperature of 330° C. in the bed, the carbon monoxide conversion is 89% and the methane selectivity 95% in the initial state. After 2000 h of run, the conversion is only 70.5%, the selectivity being 96%.

EXAMPLE 3

The conditions are the same as in example 2, but the reactor diameter is 4.7 cm and the height of the catalyst bed is 89 cm. The superficial velocity of the gas is 3.1 cm/s, that of the liquid 3.3 cm/s.

In this example, the conversion of carbon monoxide is 97% and the selectivity 95% in the initial state. After 2000 h of run, the conversion is 86% and the selectivity 96%.

EXAMPLE 4

The size of the catalyst bed, the temperature, the pressure and the feed rate of the CO+$H_2$ mixture are the same as in example 1, but the gas mixture comprises 33% of CO and 66% of $H_2$ by mole.

Under these conditions, the carbon monoxide conversion amounts to 95% and the methane selectivity to 73%.

EXAMPLES 5 TO 7

The reactor is of the same type as in examples 1 to 4. The gas and the liquid phase are circulated downwardly through the catalyst in fixed bed.

EXAMPLE 5

The reactor has a diameter of 2.5 cm and a height of 1 meter. The synthesis gas is a mixture of 33% carbon monoxide with 67% hydrogen.

The feed rate of the injected gas is 1.7 m³/h under normal conditions of temperature and pressure, giving a superficial velocity of 3.2 cm/s at 273° C., the experimental temperature, and 6 MPa.

The liquid phase is a $C_{10}$-$C_{16}$ desulfurized paraffinic hydrocarbons cut, although an alcohol fraction with a specific gravity of 0.85 at 20° C. can also be used. Its feed rate at 20° C. is about 42 l/h, thus about 57 l/h at 273° C., corresponding to a superficial velocity of 3.2 cm/s.

The catalyst of composition $Cu_1\ Co_{0.5}\ Cr_{0.4}\ Al_{0.6}\ Na_{0.1}$ is prepared by co-precipitation of a solution of copper, cobalt, chromium and aluminum nitrates with a sodium carbonate solution, washing and alcalinisation with a $Na_2CO_3$ solution of the product, which is then dried at 150° C. for 24 h, calcination at 350° C. for 4 h and shaping to 5×5 mm pellets.

400 ml of this catalyst (360 g) are introduced into the reactor.

The total carbon monoxide conversion is 27%, including 9.5% to $CO_2$.

The selectivity to alcohols is 88%, carbon dioxide being not taken into account; the remainder was converted to $CH_4$ and $C_2$+ hydrocarbons.

The distribution of the alcohols was the following (in % b.w.): $C_1$: 37% $C_2$: 34% $C_3$: 17% $C_4$: 6% $C_5$+: 6%.

EXAMPLE 6

(Comparison)

The reactor, the catalyst and the gas are the same as above, but the injection rate is only 0.6 m³/h under the normal conditions of temperature and pressure, corresponding to a superficial velocity of 1.1 cm/s at 273° C., experimental temperature, and 6 MPa.

The weight of the catalyst is 141 g, so that the contact time is the same as in the preceding example.

The liquid phase is the same as in example 5; its feed rate, determined at 20° C., is about 17 l/h, corresponding to a superficial velocity of 1.3 cm/s under the experimental conditions (273° C. and 6 MPa).

The total conversion of carbon monoxide is 22%, including 7.6% to $CO_2$.

The selectivity to alcohols, carbon dioxide being not taken into account, is 85%, the remainder being converted to $CH_4$ and $C_2$+ hydrocarbons.

The alcohol distribution is the following as % b.w.: $C_1$=38% $C_2$=33% $C_3$=16.5% $C_4$=6.5% $C_5$+=6%.

EXAMPLE 7

The gas comprises 25% of CO and 75% of $H_2$ and the reactor has a diameter of 2 cm and a height of 1 meter. The gas feed rate is 0.8 Nm³/h, corresponding to a superficial velocity of 3.1 cm/s at 260° C., experimental temperature, and a pressure of 4.5 MPa.

The feed rate of the liquid phase at 20° C. is about 28 l/h, corresponding to a superficial velocity of 3.2 cm/s under the experimental conditions.

Under these conditions, the conversion of CO is 14.9%, the selectivity to methanol 73%, the selectivity to $CO_2$ 26% and the selectivity to $CH_4$ and other hydrocarbons 1%.

What is claimed is:

1. In a process for synthesizing hydrocarbons or alcohols, comprising reacting carbon monoxide with hydrogen, in the presence of a catalyst for synthesis of hydrocarbons or alcohols, and in the presence of an inert diluent, the improvement comprising downwardly flowing the carbon monoxide and hydrogen, as a gas phase, in admixture with a liquid phase of said inert diluent, through a reaction zone comprising a fixed bed of said catalyst, the superficial velocities of the gas phase and of the liquid phase each being at least 1.5 centimeters per second under the temperature and pressure conditions of the reaction.

2. A process according to claim 1, wherein the superficial velocities are both between 3 and 20 cm/s.

3. A process according to claim 1, wherein the catalyst is a catalyst for the synthesis of methane.

4. A process according to claim 1, wherein the catalyst is a catalyst for the synthesis of alcohols.

5. A process according to claim 1 wherein the inert diluent has a density of 0.4 to 2 g/cm³ and a viscosity of 0.05 to 10 mPa.s under the reaction conditions.

6. A process according to claim 1, wherein the inert diluent is a hydrocarbon or a hydrocarbon fraction.

7. A process according to claim 1, wherein the inert diluent is a heavy alcohol or a mixture of heavy alcohols.

8. A process according to claim 1, wherein the catalyst particles have an average diameter of 1 to 6 mm.

9. A process according to claim 3, wherein the catalyst comprises nickel.

10. A process according to claim 1, wherein 1.5-4 moles of hydrogen per mole of carbon monoxide are fed to the reaction zone.

11. A process according to claim 1, wherein the reaction is effected at a temperature of 200°-400° C. and a pressure of 1-20 MPa.

* * * * *